United States Patent [19]

Harshman

[11] Patent Number: 4,615,884
[45] Date of Patent: Oct. 7, 1986

[54] METHOD AND VACCINE FOR TREATMENT OF DEMYELINATING DISEASES

[75] Inventor: Sidney Harshman, Nashville, Tenn.

[73] Assignee: Vanderbilt University, Nashville, Tenn.

[21] Appl. No.: 721,841

[22] Filed: Apr. 9, 1985

[51] Int. Cl.[4] ............................................. A61K 39/085
[52] U.S. Cl. ...................................... 424/92; 530/403; 530/405; 530/825; 435/882; 435/883
[58] Field of Search ....................... 260/112 R; 424/92; 530/403, 405, 825; 435/882, 883

[56] References Cited

PUBLICATIONS

J. Bacteriology, 96, 1429–1430 (1966), Bernheimer et al.
Biochem. 12, 2672–2677 (1973), Six et al.
Science, 191, 380–383 (1976), Bock et al.
Canadian Journal of Microbiology, 25, 686–692 (1979), Lo et al.
Molecular & Cellular Biochem. 23, 143–152 (1979), Harshman.
Pharmacol. Ther. 19, 55–106 (1983), Freer et al.

*Primary Examiner*—Howard E. Schain
*Attorney, Agent, or Firm*—Tilton, Fallon, Lungmus & Chestnut

[57] ABSTRACT

Inactivated staphylococcal alpha toxin which is in a detoxified immunogenically active form prepared as a vaccine and administered parenterally to patients having multiple sclerosis or other disease involving demyelination of nerve sheath myelin. The amount of the inactivated alpha toxin administered is sufficient to effectively immunize the patient against active staphylococcal alpha toxin. The patient becomes subsequently infected with staphylococcus, the alpha toxin resulting from the infection is neutralized by the alpha toxin binding antibodies. This prevents exacerbation of the demyelination of the nerve sheaths, which otherwise can be promoted by the alpha toxin resulting from the staphylococcus infection.

8 Claims, No Drawings

METHOD AND VACCINE FOR TREATMENT OF DEMYELINATING DISEASES

FIELD OF INVENTION, BACKGROUND, AND PRIOR ART

The field of this invention is the treatment of demyelinating diseases such as multiple sclerosis. More specifically, the invention is concerned with a method and vaccine for protecting against exacerbation of nerve sheath demyelination.

There is a class of human diseases of the nervous system which although varying in etiology involve progressive injury to nerve sheath myelin. These conditions are therefore sometimes referred to as demyelinating diseases. The most prevalent such disease is multiple sclerosis, but other such diseases include the Landy-Guillan-Barre Syndrome, Krabbe's Disease, and Alzheimer's Disease. Myelin sheath injury may occur in both the peripheral and central nervous system including the brain. As demyelination proceeds, there is progressive interference with nerve transmission.

Staphlococcal alpha toxin ($\alpha$-toxin) is an extracellular protein produced by pathogenic strains of Staphylococcus. Freer, et al. (1983), Pharmacol. Ther. 19: 55–106. This toxin has been isolated in pure form, and a number of its physical and chemical characteristics determined: Cassidy and Harshman (1976), Infect. Immun. 13: 982–986; Six and Harshman (1973), Biochemistry, 12: 2672–2683. Alpha toxin is distinguished biologically by its selective hemolytic activity, its ability to cause spastic paralysis in muscle, and its lethality for most laboratory animals.

It has been suggested that alpha toxin may play a part in the cause and/or aggravation of multiple sclerosis. Harshmann, Molecular & Cellular Biochem., (1979), 23: 143–152. This reference describes experiments evidencing that staphyloccal alpha toxin binds to isolated rabbit vagus nerves resulting in disorganization of the myelin sheaths as the first symptom of injury to peripheral nerves. The reference also describes in vivo studies in which alpha toxin was injected into mice brains resulting in collective disruption of the myelin sheaths in the central nervous system. Harshman observed that an alpha toxin-animal system may be "a possible laboratory model for multiple sclerosis," and that alpha toxin "may play a role in the etiology of multiple sclerosis in man."

SUMMARY OF INVENTION

This invention is based on a novel concept for the treatment of human patients having diseases involving demyelination of nerve sheath myelin. More specifically, this invention envisions a method of protecting against exacerbation of demyelination by parenterally administering to the patient staphylococcal alpha toxin in a detoxified immunogenically active form.

In a preferred embodiment of the method, the amount of detoxified alpha toxin administered is sufficient to effectively immunize the patient against active staphylococcal alpha toxin. Following such immunization, if the patient afflicted with multiple sclerosis or other demyelinating disease acquires a staphlyococcal infection, the active alpha toxin resulting from the infection will be neutralized by the antibodies produced by the immunization. This will largely prevent the active alpha toxin from exacerbating injury to the myelin nerve sheaths.

For practicing the method of this invention, a parenterally administerable vaccine is employed. Preferably the vaccine is adapted for intramuscular injection (I.M.). The I.M. vaccine may comprise a sterile aqueous solution and/or dispersion of inactivated staphylococcal alpha toxin. The term "inactivated" refers to elimination of toxicity but not antigenicity. The vaccine may be prepared in convenient individual dose form. Preferably, each dose will contain at least 0.5 to 2.0 milligrams (mg) of the inactivated toxin.

DETAILED DESCRIPTION

Staphylococcal alpha toxin ($\alpha$-toxin) can be recovered from cultures of Staphylococcus aureus. One convenient procedure referred to as the "pore glass bead procedure" is described by Cassidy and Harshman (1976), Infect. Immun. 13: 982–986. Purification of the alpha toxin is obtained by adsorption chromatography on glass beads. Other references describing recovery and purification of alpha toxin are: Six and Harshman (1973), Biochem., 12: 2672–2677; Bock et al. (1976), Science, 191:380–383; and Watanabe et al. (1974), Japan, J. Exp. Med. 44: 167–178. Bernheimer and Schwartz (1963), J. Gen. Microbiol., 30:455, summarized and discussed alpha toxin purification procedures prior to 1963.

The activity of the recovered alpha toxin may be measured in terms of hemolytic units (H.U./mg protein). The procedure for determining hemolytic potency is described by Bernheimer and Schwartz (1963), J. Gen. Microbiol., 30: 455–468. Rabbit red blood cells are employed for determining the specific hemolytic activity. The protein may be measured either by the Coomassie Blue procedure of Bradshaw (1976), Anal. Biochem., 72: 248–254, or by the method of Lowry et al. (1951), J. Biol. Chem., 193: 265–275. The activity of the recovered and purified alpha toxin can range from about 20,000 to 40,000 H.U./mg protein.

Six and Harshman have shown that there are two forms of staphylococcal alpha toxin. Biochem., (1973) 12: 2672–2677. However, the A and B forms have similar molecular sizes (approximately 28,000 mol. wt.) and may be recovered together in purified form. Further, the two forms are homogeneous and immunochemically identical. For the purposes of the present invention, both forms are equivalent, and the term "alphatoxin" is used to refer to both forms generically. In practicing the present invention, the alpha toxin, after recovery in its active hemolytic form, is inactivated or detoxified to render the alpha toxin non-hemolytic while preserving its antigenicity. Staphylococcal alpha toxin in such a detoxified immunogenically active form may be prepared either by formalin or heat inactivation. These procedures have been described in the alpha toxin literature. For formalin inactivation, see, for example, Bernheimer, et al. (1966), J. Bacteriol. 96: 1429–1430; and for heat inactivation, see Lo and Fackrell (1979), Chem. J. Microbiol., 25: 686–692.

The inactivated alpha toxin may be either soluble or insoluble. Usually both soluble and insoluble forms will be present. The soluble, hemolytically inactive complex is referred to as the 12-S form, and is a hexamer, ringlike structure made up of six 3S monomers. Insoluble alpha toxin is in the form of a random coil which is devoid of organized structure. Depending on the amount of aggregation of the inactivated molecules, insolubilized alpha toxin may be formed and will appear as a more or less turbid dispersion. Detoxified, immunogenically active alpha toxin in either its soluble or insoluble forms is biologically stable. While renaturation can be obtained under certain special laboratory conditions, such renaturation conditions are not encountered in parenteral administration.

By way of specific example, active alpha toxin can be treated for heat inactivation in a 0.05M phosphate buffer at pH 7.2. A typical concentration for this treatment is about 4 mg/ml. Detoxifying inactivation can be achieved by heating for 60–75 minutes at 56° C., or more rapidly, in 6–7 minutes at 100° C. Inactivation can be confirmed by measuring the loss in hemolytic activity against rabbit red blood cells, using the method of Bernheimer and Schwartz cited above. Retained immunogenicity can be confirmed by the reactivity of the inactivated alpha toxin to anti-sera to active alpha toxin.

Although rendered essentially non-toxic by heat or formalin treatment as described above, the detoxified alpha toxin remains immunogenically active. The antigenic sites of the molecule are not modified or destroyed by the inactivation. The detoxified alpha toxin may be safely administered to humans in sufficient amounts to produce antibodies which will bind to and neutralize active alpha toxin.

The inactivated alpha toxin can be conveniently administered n by parenteral injection, preferably by intramuscular injection. Vaccines for use for this purpose may consist of sterile aqueous solutions and/or suspensions of the inactivated toxin. No adjuvant is required but one may optionally be included if safe for human administration. For example, suspension concentrations may range from about 0.25 to 10.0 mg/ml. Sterilization of the vaccine may be obtained by millipore filtration using a 0.22 μm filter, preferly before inactivation. Such filtration will also remove protein aggregates that might interfere with passage through a small gauge needle.

A sufficient amount of the detoxified alpha toxin should be parenterally administered to effectively immunize the patient against active staphylococcal alpha toxin. Dose sizes per injection may range from 0.3 to 3.0 milligrams (mg) of the alpha toxin. The desired dose will usually comprise at least 0.5 to 2.0 mg toxin. The immunization protocol may consist of an initial sensitizing dose followed several weeks later (e.g. one month) by an immunizing dose. If needed, as with young children, a further immunizing dose may be given after another month. Dose sizes may be the same for the sensitizing and immunizing injections. Reinforcement doses may be given annually or more often as needed. The objective will be to maintain a level of circulating antibodies to alpha toxin sufficient to neutralize the active alpha toxin resulting from subsequently-acquired staphylococcal infection. Effective antibody titers can be determined by testing the serum of the patient.

I claim:

1. In the treatment of human patients having diseases involving demyelination of nerve sheath myelin, the method of protecting against exacerbation of the demyelination, comprising parenterally administering to the patient staphylococcal alpha toxin in a detoxified, immunogenically active form, the amount administered being effective to immunize the patient against active alpha toxin resulting from a staphylococcal infection.

2. The method of claim 1 in which the disease is multiple sclerosis.

3. The method of claim 1 in which said detoxified alpha toxin is administered in dose amounts of from 0.3 to 3.0 milligrams of alpha toxin per dose.

4. In the treatment of human patients having multiple sclerosis, the method of protecting against exacerbation of nerve sheath demyelination, comprising parenterally administering to the patient staphylococcal alpha toxin in a detoxified, immunogenically active form, at least from 0.5 to 2.0 milligrams (mg) of the detoxified alpha toxin being administered for immunizing the patient against active staphylococcal alpha toxin.

5. The method of claim 4 in which at least two sequential doses of said detoxified alpha toxin are administered to provide a first sensitizing dose followed by at least one immunizing dose.

6. A vaccine in parenterally administrable dose form for use in treating patients having multiple sclerosis or other demyelination disease, comprising a sterile aqueous solution and/or dispersion of staphylococcal alpha toxin in detoxified, immunogenically active form.

7. The vaccine of claim 6 consisting of a single dose containing from 0.3 to 3.0 milligrams of said detoxified alpha toxin.

8. A vaccine in parenterally administrable dose form for use in treating patients having multiple sclerosis, comprising a sterile aqueous solution and/or dispersion of staphylococcal alpha toxin in detoxified immunogenically active form, said dose form consisting of a single dose containing from 0.5 to 2.0 milligrans of (mg) of said detoxified alpha toxin.

* * * * *